United States Patent [19]

Ewers

[11] 4,071,022
[45] Jan. 31, 1978

[54] ORTHOPEDIC ARM SLING
[75] Inventor: Marion H. Ewers, Payson, Ariz.
[73] Assignee: Air Rotor Development Company, Inc., Payson, Ariz.
[21] Appl. No.: 735,306
[22] Filed: Oct. 26, 1976
[51] Int. Cl.² .............................................. A61F 5/40
[52] U.S. Cl. .................................................. 128/94
[58] Field of Search ............................ 128/94, 83, 82
[56] References Cited

U.S. PATENT DOCUMENTS

| 980,464 | 1/1911 | Wermuth | 128/94 |
|---|---|---|---|
| 1,266,688 | 5/1918 | Kassner | 128/94 |
| 3,103,216 | 9/1963 | Scott | 128/94 |
| 3,433,221 | 3/1969 | Kendall et al. | 128/94 |

Primary Examiner—John D. Yasko
Attorney, Agent, or Firm—Charles E. Cates

[57] ABSTRACT

An orthopedic arm sling made of a lightweight fabric material which has a front apron, the bottom of which is secured to the top to form a cradle extending the length of the arm. The supporting straps extend over the shoulders, cross the wearer's back and engage the edges of the apron to secure the apron and the arm to the wearer's body and keep the weight from being borne by the neck of the wearer. Optionally a restraint strap secures the arm from horizontal movement.

10 Claims, 3 Drawing Figures

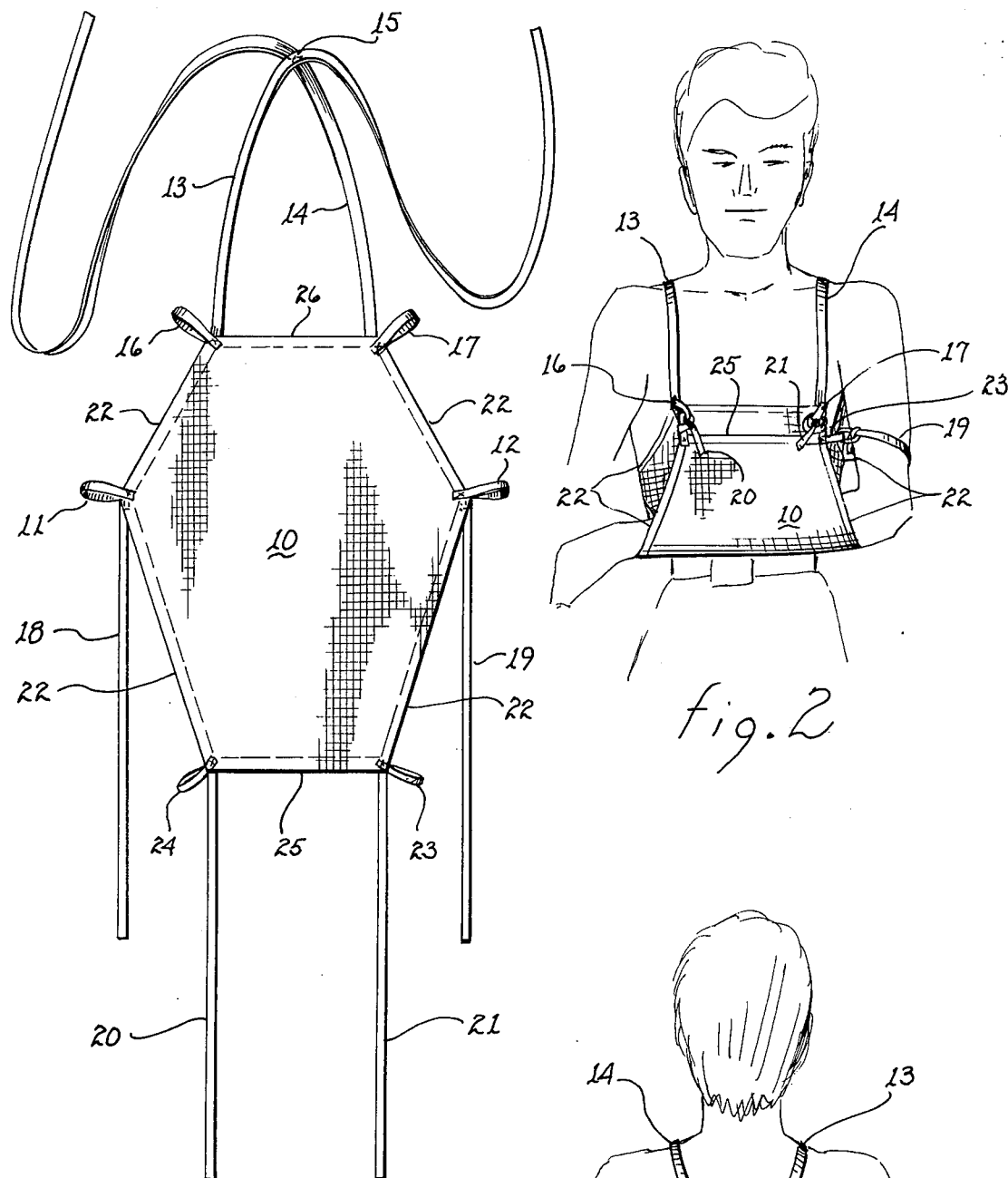
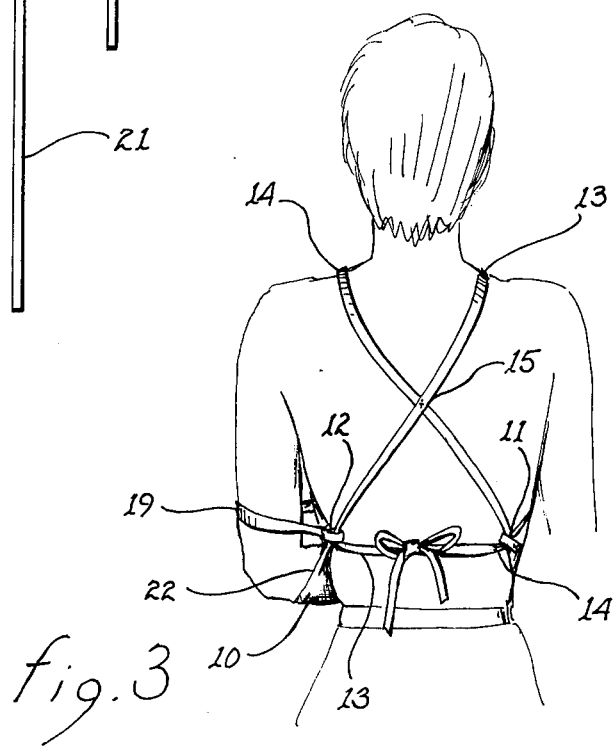
fig. 1
fig. 2
fig. 3

ORTHOPEDIC ARM SLING

BACKGROUND OF THE INVENTION

This invention relates to flexible orthopedic arm slings.

The common occurrence of the broken arm has generated a number of orthopedic arm sling configurations. These configurations while providing support for the damaged arm at the same time either cause discomfort to the wearer, fail to secure the arm to the body so as to substantially immobilize it, fail to fully support the arm along its length or require fastening to an article of the wearer's clothing.

The most common configuration of an orthopedic arm sling extends around the neck of the wearer and consequently the entire weight of the arm along with that of any brace or cast associated therewith is borne by the neck. This problem has been recognized and several configurations have been utilized wherein straps are utilized in place of a sling-like supporting member. In these different attempts to alleviate the bearing of the weight of the arm, a number of different inconveniences to the wearer have arisen.

Accordingly, it is an object of the present invention to provide an improved lightweight arm sling wherein support is provided along the length of the arm and the arm is urged against the body of the wearer to substantially immobilize the arm.

A further object of this invention is to provide a lightweight fabric sling that is inexpensive to manufacture, provides that the load is not borne by the neck of the wearer and is not attached to the clothing of the wearer for support.

Still another object of this invention is to provide a lightweight sling that can be made entirely of fabric and is capable of being used for either arm.

SUMMARY OF THE INVENTION

The present invention is directed to the provision of a lightweight orthopedic arm sling which includes a flexible arm cradle that is supported on the chest of the wearer by first supporting means comprising two straps each of which extends over one shoulder of the wearer.

These supporting straps cross and preferably are held together by coupling means located on the back of the wearer, extending beyond and away from the cross or coupling means to engage first fastening means. The first fastening means are connected to the flexible support at two spaced locations proximate to the arm to be supported and each location receives a supporting strap. In preferred embodiments of the invention, the supporting straps have a length sufficient to extend from the first fastening means to behind the back of the wearer. The free ends of these supporting straps are then tied to provide an increased urging of the arm being supported against the body of the wearer.

A second fastening means is secured to the flexible support means at the upper edge of the apron proximate to one or more fixed points of attachment of the first supporting means straps. It is also utilized in one preferred embodiment to attach to second support means causing the apron to form a lightweight flexible cradle that conforms to the contour of the wearer's damaged arm or the apparatus associated with it. The second supporting means is connected to the apron at one or more spaced locations proximate to its lower edge which is opposite the point of attachment of the first supporting means. In use, the second support means is fastened at one or more locations to second fastening means to provide an arm support that extends along substantially the entire length of the arm.

Restraining straps are connected to the apron proximate to the points of attachment of the first fastening means. The restraining straps each have a length sufficient to extend around the upper arm of the wearer and engage second fastening means, or alternatively, third fastening means attached to the lower edge of the apron. Depending on the arm injured one or the other restraining strap is used to secure the arm of the wearer against movement in a direction substantially parallel to the arm being supported.

The foregoing description is directed to an orthopedic arm sling that is lightweight and can be manufactured from a fabric material with a resultant low cost of production. The sling is readily washable when made from a cotton fabric and occupies a small volume when stored.

Further features and advantages of the invention will become more readily apparent from the following detailed description of a specific embodiment of the invention when taken in conjunction with the accompanying drawings.

BRIEF DESCRIPTION OF THE DRAWINGS

FIG. 1 is a plan view of an embodiment of the invention.

FIG. 2 is a front view of the embodiment of FIG. 1 as applied.

FIG. 3 is a back view of the embodiment of FIG. 1 as applied.

DETAILED DESCRIPTION OF THE PREFERRED EMBODIMENT

Referring now to FIG. 1, the invention is shown in plan view as comprising a fabric material apron 10 which in usage forms the flexible cradle for the arm of the wearer.

First support means comprising straps 13 and 14 are connected to apron 10 at spaced locations on the upper portion. The apron is fabric, preferably cotton and the straps are also fabric. As shown in FIG. 1, straps 13 and 14 are integral with the edging material 22 for apron 10. This form of construction is preferred since the straps 13 and 14 are major load bearing elements of the orthopedic arm sling and the load is now distributed over a greater area.

Straps 13 and 14 are fastened together by coupling means 15 which in the embodiment of FIG. 1 is a series of stitches. However, it should be recognized that an adjustable slide or ring may be utilized if desired. The straps 13 and 14 are thus drawn together on the back of the wearer.

Second support means which may be either third or fourth supporting straps 20, 21, or both, are connected to apron 10 at spaced locations on the lower edge 25 of the apron. Turning to FIG. 2 it is noted that the arm to be supported is placed in apron 10 and that the straps 20 and 21 are fastened to third and fourth fastening loops 16 and 17 to provide the flexible cradle of the invention. Loops 16 and 17 are secured to the edge of apron 10 by stitching and are formed of the same material as edging 22. Second support means may alternatively be one strap at the lower edge of the apron engaging one loop or other fastening means at the upper edge 26 of the apron 10.

First and second fastening loops 11 and 12 are secured to the edge of apron 10 at opposite sides thereof and as shown in FIG. 2 the loops are proximate to the arm being supported. These loops are preferably secured to the edge of apron 10 by stitching and receive supporting straps 13 and 14 respectively when the present invention is applied.

First and second restraining straps 18 and 19 are secured to the edge of apron 10 proximate to fastening loops 11 and 12 respectively. Straps 18 and 19 are stitched on to the edging 22. One is utilized to substantially reduce movement of the supported arm in a direction across the front of the body or substantially parallel to the arm itself and the other is cut off or tucked into the cradle.

In an example of use the invention is shown as applied to the left arm of a wearer in the front and back views of FIGS. 2 and 3. As shown in FIG. 2, apron 10 forms the flexible support for the arm by the fastening of supporting straps 20 and 21 to loops 16 and 17 respectively. Supporting straps 13 and 14 extend over the shoulders of the wearer and are shown crossing in FIG. 3 due to the stitches 15 which couple them together on the back of the wearer. These supporting straps 13 and 14 pass through loops 12 and 11 respectively and are then tied behind the lower portion of the back of the wearer. This sling removes the load of the arm and any other apparatus associated therewith from the neck of the wearer and places it essentially equally on the shoulders.

The straps 13 and 14 also serve to hold the arm of the wearer against his body to inhibit movement outwardly of the body. In addition, restraining strap 19 affixed to apron 10 at the edging 22 is drawn over the upper portion of the supported arm around to the front and is fastened to loop 17 or to loop 23 (FIG. 1) to inhibit movement of the arm in a direction substantially parallel to the arm. If the wearer's right arm is to be supported, strap 18 would be fastened to loop 16 or 24 instead of loop 17 or 23. In use the other restraining strap is cut off or tucked into the cradle.

a decided advantage in this device is that by pulling up the straps 13, 14 the support means 10 is raised thereby raising and immobilizing the injured arm and its shoulder. A fine adjustment can be made by tightening or loosening the strap 21. If the other arm were the injured one, strap 20 would be adjusted instead.

This embodiment of the present invention is shown fabricated of cotton material without the use of other materials. Thus it is lightweight, readily washable, durable, and does not require expensive steps to manufacture. While the above description has referred to a specific embodiment, it is recognized that modifications and variations may be made therein without departing from the spirit and scope of the invention.

What is claimed is:
1. An orthopedic arm sling which comprises:
   a. A flexible apron having upper and lower edges forming a cradle for receiving an arm and providing support therefor along a substantial portion of the arm, said cradle maintaining the arm against the body of the wearer;
   b. First support means comprising straps connected to the upper edge of said apron at spaced locations proximate to the body of the wearer, said straps adapted to extend over the shoulders of the wearer;
   c. First fastening means connected to said apron at spaced locations proximate to the arm to be supported for engaging and securing said straps;
   d. Second support means attached to the lower edge of said apron;
   e. Second fastening means proximate said first support means connecting said upper and lower edges of said apron by engaging said second support means to form a cradle.
2. The orthopedic arm sling of claim 1 further comprising coupling means engaging said supporting straps for drawing the straps together on the back of the wearer.
3. The orthopedic arm sling of claim 1 further comprising a restraining strap connected to said cradle proximate said first fastening means, said restraining strap having a length sufficient to extend around the upper arm of the wearer and engage second fastening means whereby the arm of the wearer is secured against movement substantially parallel the length thereof.
4. The orthopedic arm sling of claim 1 further comprising third fastening means attached to said cradle proximate said second support means and a restraining strap connected to means proximate to the first fastening means, said restraining strap having a length sufficient to extend around the upper arm of the wearer and engage said third fastening means.
5. The orthopedic arm sling of claim 1 wherein said apron is formed of a fabric material and wherein said second means comprises two straps connected to said apron at spaced locations proximate to the lower edge of said apron, said two straps having a length sufficient to be connected to said second fastening means, comprising two loops fastened to the upper edge of said apron.
6. The orthopedic arm sling of claim 3 wherein said first, second and third fastening means each comprise loops for receiving a supporting strap.
7. The orthopedic arm sling of claim 1 wherein said first support means have a length sufficient to extend from the apron over the shoulders of the wearer, through the coupling means and said first fastening means to permit mutual engagement thereof behind the back of the wearer.
8. The orthopedic arm sling of claim 7 wherein said coupling means secures said first support means in a fixed relationship to form a loop which is placed over the head of the wearer.
9. The orthopedic arm sling of claim 8 wherein the support means are formed of a fabric material.
10. The orthopedic arm sling of claim 9 wherein said first fastening means are secured substantially at the midpoints of opposing sides of said apron.

* * * * *